of an acylating agent, a cobalt and/or manganese compound and a compound which donates bromide, ions, and subsequently hydrolysing the products in a conventional manner. In the presence of the acylating agent, a selective oxidation of the hydroxyl-substituted aromatic compounds to carboxylated hydroxy compounds, which are obtained in a good state of purity and yield, is obtained without the application of pressure.

United States Patent [19]

Clausen et al.

[11] Patent Number: 5,041,634

[45] Date of Patent: Aug. 20, 1991

[54] PROCESS FOR THE PREPARATION OF CARBOXYLATED AROMATIC HYDROXY COMPOUNDS

[75] Inventors: Martin Clausen; Paul Rys; Junkuan Wang, all of Zurich, Switzerland

[73] Assignee: Ciba-Geigy Corporation, Ardsley, N.Y.

[21] Appl. No.: 278,395

[22] Filed: Dec. 1, 1988

[30] Foreign Application Priority Data

Dec. 9, 1987 [CH] Switzerland .................. 4799/87-4

[51] Int. Cl.$^5$ ............................................. C07C 51/16
[52] U.S. Cl. ................................. 562/416; 562/412; 562/421
[58] Field of Search ................... 562/421, 412, 416

[56] References Cited

U.S. PATENT DOCUMENTS 4,740,614  4/1988  Fjare ................................. 562/416

*Primary Examiner*—Paul J. Killos

*Attorney, Agent, or Firm*—Kevin T. Mansfield; Edward McC. Roberts

[57] ABSTRACT

Process for the preparation of compounds of the formula HO-Ar-COOH in which Ar is a substituted or unsubstituted aromatic ring system, by oxidizing, by means of oxygen or compounds which donate oxygen, compounds of the formula HO-Ar-$R_1$ in which $R_1$ is alkyl having 1 to 5 carbon atoms and Ar is as defined above, or the O-acyl derivatives of these compounds, in an organic solvent at 80° to 130° C. and in the presence of an acylating agent, a cobalt and/or manganese compound and a compound which donates bromide, ions, and subsequently hydrolysing the products in a conventional manner. In the presence of the acylating agent, a selective oxidation of the hydroxyl-substituted aromatic compounds to carboxylated hydroxy compounds, which are obtained in a good state of purity and yield, is obtained without the application of pressure.

The compounds obtained in accordance with the process are, for example, valuable intermediates for the preparation of dyes, plastics and pharmaceuticals.

14 Claims, No Drawings

PROCESS FOR THE PREPARATION OF CARBOXYLATED AROMATIC HYDROXY COMPOUNDS

The present invention relates to a novel, improved process for the preparation of carboxylated aromatic hydroxy compounds, in particular carboxylated phenols or naphthols, by selective catalytic oxidation of the corresponding alkyl-substituted aromatic hydroxy compounds.

The oxidation of alkyl-substituted aromatic compounds in the presence of catalysts is already known. Thus, for example, EP-A 204,119 describes a process for the preparation of 2,6-naphthalenedicarboxylic acid by the oxidation of 2,6-diisopropylnaphthalene in the presence of an oxidation catalyst containing the components cobalt/manganese/alkali metal/bromide, the reaction being carried out under pressure in acetic acid and/or propionic acid.

It has now been found that it is possible to prepare carboxylated aromatic hydroxy compounds selectively by the catalytic oxidation of alkyl-substituted aromatic hydroxy compounds, if the reaction is carried out in a suitable solvent and in the presence of an acylating agent.

The present invention therefore relates to a process for the preparation of compounds of the formula $$\text{HO-Ar-COOH}, \qquad (1)$$

in which Ar is a substituted or unsubstituted aromatic ring system, preferably substituted or unsubstituted phenylene or naphthylene, which comprises oxidizing, by means of oxygen or oxygen donors, compounds of the formula $$\text{RO-Ar-R}_1 \qquad (2)$$

in which R is hydrogen or $R_2CO-$ in which $R_2$ is hydrogen or $C_1-C_4$alkyl, $R_1$ is alkyl having 1 to 5 carbon atoms and Ar is as defined above, in an organic solvent at 80° to 130° C. and in the presence of an acylating agent, a cobalt and/or manganese compound and a compound which donates bromide ions, and subsequently hydrolysing the products in a conventional manner.

The present invention also relates to the carboxylated aromatic hydroxy compounds prepared in accordance with the process and to the use thereof as intermediates for the preparation of, for example, dyes, plastics (polymers) or pharmaceuticals; further the compounds are also suitable for use as colour developers in pressure-sensitive and heat-sensitive recording material.

The compounds of the formula (2) employed in the process according to the invention are mononuclear or polynuclear, for example dinuclear or trinuclear, aromatic compounds which are substituted as indicated, preferably aromatic compounds belonging to the group of benzenes and naphthalenes.

The alkyl substituents $R_1$ contain 1 to 5, preferably 1 to 3, carbon atoms and are, for example, methyl, ethyl, n-propyl, isopropyl, n-butyl, isobutyl, sec-butyl, tert-butyl and pentyl and isomers thereof; methyl, ethyl and especially isopropyl are preferred.

The compounds of the formula (2) can optionally contain further substituents, for example halogen, in particular chlorine, cyano, nitro, sulfo and $C_1-C_4$alkoxy.

The compounds of the formula (2) preferably have the formula $HO-Ar-R_1$, in which Ar and $R_1$ are as defined above, especially the formulae

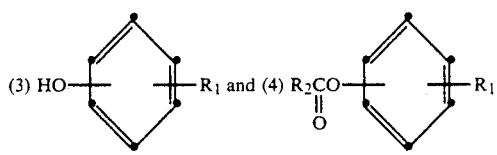

or

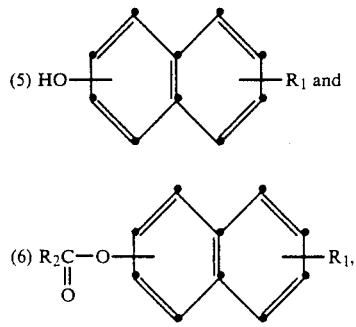

in which $R_1$ is as defined above and $R_2$ is hydrogen or $C_1-C_4$alkyl, in particular $C_1-C_3$alkyl and preferably $CH_3$, and is also phenyl.

Preferred examples of the compounds of the formulae (3) and (5) are p-methylphenol or p-isopropylphenol and 2-methyl-6-hydroxynaphthalene or 2-isopropyl-6-hydroxynaphthalene and $R_2$-CO derivatives thereof, preferably the acetyl derivatives [formulae (4) and (6) in which $R_1$ is methyl or isopropyl and $R_2$ is methyl].

The compounds of the formulae (2) to (6) are known and can be prepared by known processes, for example by the oxidation of corresponding dialkylsubstituted aromatic compounds and the subsequent conventional hydrolysis of the monohydroperoxides formed as intermediates. The O-acyl compounds can then be prepared by a conventional acylation process from the hydroxy compounds thus obtained.

Suitable solvents for carrying out the process according to the invention are those which are stable under the reaction conditions, preferably low-molecular alkylcarboxylic acids having 1 to 5, preferably 2 to 4, carbon atoms. These are employed as indicated in combination with an acylating agent, preferably the anhydrides of the organic acids mentioned. Examples of suitable acids are formic, acetic, propionic, butyric and valeric acid, and optionally also the halogenoacetic acids. However, acetic acid or the combination acetic acid/acetic anhydride is very particularly preferred. Optionally, a combination of this type can also include other solvents which are stable to oxygen under the reaction conditions.

Suitable oxidation catalysts are composed of the oxides, hydroxides or inorganic or organic salts of cobalt and/or manganese and of compounds which donate bromide ions, such as bromine, hydrobromic acid, inorganic bromides or organic bromine compounds.

Inorganic cobalt and/or manganese salts are preferably the corresponding halides, for example the chlorides and especially the bromides, and also the carbonates, sulfates and phosphates; suitable organic salts are those of aliphatic carboxylic acids having, for example, 1 to 4 carbon atoms, such as formates, acetates, propionates, lactates, or butyrates, and also those of aromatic acids, such as benzoic or naphthoic acid. The bromides and the acetates of cobalt and manganese are particularly preferred.

Suitable compounds which donate bromide ions are inorganic and organic bromine compounds which dissolve in the reaction medium (a combination of an acid and an acid anhydride) and are capable of forming bromide ions. $Br_2$, HBr, the alkali metal bromides, such as lithium bromide, sodium bromide or potassium bromide, heavy metal bromides, such as especially cobalt bromide and manganese bromide, and also ammonium bromide, lower alkyl bromides, such as methyl bromide, ethyl bromide or bromoform, lower alkylene bromides, such as ethylene bromide, and bromides of lower carboxylic acids, such as bromoacetic acid or tribromoacetic acid, may be mentioned.

Hydrobromic acid and the alkali metal bromides and heavy metal bromides mentioned and also ammonium bromide, ethyl bromide and bromoacetic acid are preferred.

If the cobalt and/or manganese compounds (salts) are employed in the form of bromides, it is, as a rule, not necessary to employ additionally a so-called compound which donates bromide ions.

As a rule, the cobalt or manganese salts are each employed in amounts of about 2 to 4 mole %, preferably 2 to 3 mole %, relative to 1 mole of the compounds of the formula (2).

If a mixture of cobalt and manganese salts is used, the amount of this mixture is 4 to 8 mole %, preferably 4 to 6 mole %, relative to 1 mole of the compounds of the formula (2).

The ratio by weight of the salts in the mixture can vary within wide limits and is, for example, 1:10 to 10:1.

The amount of compounds which donate bromide ions, which are employed if the metal salts (cobalt and manganese salts) used as oxidation catalysts are not already in the form of bromides, can be smaller or larger than the amount equivalent to the metal cations (the total of cobalt and manganese cations) or can also be the same as this amount. Preferably, it should be greater than the equivalent amount. As a rule, therefore, an excess of about 10 to 20% above this equivalent amount is employed.

Optionally, it is additionally possible to employ, for the oxidation reaction according to the invention, so-called reaction initiators, for example organic free-radical formers belonging to the group of peroxides, preferably di-tert-butyl peroxide, or azo compounds thereof, for example azobisisobutyronitrile.

The amounts of these initiators can be about 0.1 to 5.0% by weight, for example 0.5 to 5% by weight, relative to the weight of the compounds of the formula (2).

Oxygen or gases containing oxygen, for example air, or compounds which split off oxygen, for example ozone, can be used as the actual oxidizing agent in the process according to the invention.

If oxygen is used as the oxidizing agent, 0.1 to 5 $m^3$, preferably 0.5 to 2.0 $m^3$, of this gas per kg of the compounds of the formula (2) and per hour is, for example, passed through the reaction mixture.

The reaction times are approximately within the range from 1 to 24, preferably 1 to 12 and particularly 4 to 8, hours. The reaction temperatures are preferably within the range from about 90° to 130° C., in particular within the range from 110° to 125° C.

If the compounds of the formulae (3) or (5) (having a free hydroxyl group) are used as the starting materials, the process according to the invention can be carried out in such a way that these compounds are dissolved in an acylating agent, in particular an acid anhydride and preferably acetic anhydride, and are then acylated. This esterification can be accelerated by adding a catalytic amount of an acid, preferably, for example, hydrobromic acid (48%), and by increasing the temperature. Complete esterification can be reached in about 30 to 60 minutes at 100° C.

Acid anhydride is converted into the free acid both during the initial acylation, preferably by means of an acid anhydride, and during the actual oxidation. Consequently, the ratio of acid anhydride to acid changes during the whole of the oxidation process.

It is therefore not necessary for the oxidation to take place solely in the acid anhydride as the reaction medium. The only important factor is that there should always be sufficient acid anhydride present as acylating agent to prevent the appearance of free hydroxyl groups during the oxidation. This is because these groups can stop the oxidation, which proceeds essentially by means of free radicals.

The actual oxidation is carried out, as a rule, by passing oxygen into the reaction solution as the oxidizing agent and then, optionally, adding the reaction initiator, preferably di-tert-butyl peroxide or azobisisobutyronitrile, and subsequently adding the catalyst with stirring. The temperature of the reaction solution during the oxidation is kept within the range indicated, preferably at 110° to 125° C. The oxidation is terminated by switching off the supply of oxygen after about 4 to 8 hours, for example after 6 hours.

The oxidation products obtained are essentially compounds of the formulae

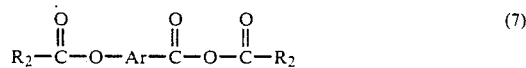

and

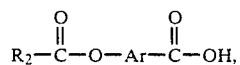

in which $R_2$ and Ar are as defined above.

The reaction mixture is then cooled to about 50° to 70° C. and hydrolysed, at the temperature indicated, in the course of about 5 to 10 hours by adding water in an amount of, for example, 15 to 20% by volume, relative to the total amount of solvent, the compounds of the formula (7) being converted virtually quantitatively into the compounds of the formula (8).

As a rule, the compounds of the formula (8) crystallize out and are thus isolated from the reaction mixture before the compounds of the formula (1) are obtained from the latter by further hydrolysis, which can be carried out either in the acid pH range (adding, for example, hydrochloric or sulfuric acid) or in the basic pH range (adding, for example, sodium hydroxide solution); the compounds of the formula (1) are then purified in a customary manner, for example by recrystallization.

As a rule, the compounds of the formula (7) remain in solution. This solution, which can also contain the catalysts or the catalyst mixture, can be employed in a further oxidation.

The process according to the invention can thus be carried out discontinuously or continuously. In the latter case the anhydride/acid ratio in the solvent-catalyst mixture after the removal of the compounds of the formula (8) must be adjusted to the desired value for re-use, as a rule either by adding fresh anhydride and/or by removing excess acid by distillation.

Both if the reaction is carried out continuously and if it is carried out discontinuously, it is also possible to begin the reaction using the O-acylated compound. The O-acylation can then be carried out previously in another reaction vessel, and, if it is advantageous, the O-acylated compound can also be isolated.

Customary analytical methods, in particular high-pressure liquid chromatography (HPLC), are used to monitor the process according to the invention and to analyse the resulting products.

The advantages of the process according to the invention are primarily that it is possible to obtain, under normal pressure, a selective oxidation (carboxylation) of compounds of the formula (2) or O-acyl derivatives thereof to give compounds of the formula (1).

A comparable oxidation in an acid (acetic acid) can, however, virtually not be carried out under the conditions according to the invention (in the absence of pressure). Only if pressure is applied is a definite reaction achieved using acetic acid as the sole solvent.

The oxidation process according to the invention affords the products according to the process at lower reaction temperatures and without the application of pressure in a markedly better state of purity and yield, compared with the known oxidation processes.

The compounds of the formula (1), optionally also in the acyloxy form compounds of the formula (S), are suitable intermediates for the preparation of, for example, dyes, as comonomers for the preparation of polymers which can, for example, be processed further to give synthetic fibres, or for the preparation of pharmaceuticals: they are also suitable, for example, as colour developers in pressure-sensitive and heat-sensitive recording materials.

The examples below illustrate the process according to the invention, but without limiting it to these examples. Parts and percentages are by weight, unless stated otherwise. The temperature is quoted in degrees centigrade.

EXAMPLE 1

5 g of 6-hydroxy-2-isopropylnaphthalene (purity 99%, HPLC), dissolved in 40 g of acetic anhydride, are put into a 100 ml four-necked flask equipped with a stirrer, a thermometer, a reflux condenser and a gas inlet frit, 3 drops of hydrobromic acid (48%) are added with stirring, and the mixture is then heated to 120° C. After a reaction time of 30 minutes at this temperature, the supply of oxygen is started at a rate of 80 ml/minute and, at the same time, 0.1 g of di-tert-butyl peroxide and 0.16 g of cobalt(II) acetate tetrahydrate and 0.2 g of manganese(II) bromide tetrahydrate are added to the reaction solution.

The reaction is terminated after 6 hours by switching off the supply of oxygen. The reaction mixture is cooled to 60° C., 7 ml of water are added, in the course of which a pH within the acid range is set up, and the mixture is hydrolysed at 60° C. for 5 to 10 hours.

After cooling to room temperature, the reaction mixture is added dropwise and with good stirring to 150 ml of ice water. The product which precipitates is separated off, washed with water and dried. Yield: 4.6 g of 6-acetoxy-2-naphthoic acid (purity: 90%, HPLC) (75% yield, relative to 6-hydroxy-2-isopropylnaphthalene).

The 6-acetoxy-2-naphthoic acid obtained can be purified further by recrystallization from water, a water/alcohol mixture or dilute acetic acid.

It can be converted into 6-hydroxy-2-naphthoic acid by hydrolysis with aqueous sodium hydroxide solution.

6-Hydroxy-2-methylnaphthalene can also be oxidized to 6-hydroxy-2-naphthoic acid analogously.

Comparison Example 1

7.8 g of 6-acetoxy-2-isopropylnaphthalene are dissolved in 40 ml of acetic acid and the mixture is put into the reaction apparatus of Example 1. The solution is heated to 110° C.; the supply of oxygen (80 ml/minute) is then started and 0.2 g of di-tert-butyl peroxide, 0.21 g of cobalt(II) acetate tetrahydrate and 0.24 g of manganese(II) bromide tetrahydrate are added, in this sequence, to the reaction solution with stirring.

After a reaction time of 6 hours only about 30% of the starting material have been converted into oxidation products.

Comparison Example 2

5 g of 6-hydroxy-2-isopropylnaphthalene are dissolved in 40 g of acetic acid and the mixture is put into the reaction apparatus of Example 1; the oxygen supply is then started and 0.2 g of di-tert-butyl peroxide, 0.17 g of cobalt(II) acetate tetrahydrate and 0.2 g of manganese(II) bromide tetrahydrate are added, in this sequence and with stirring, to the reaction solution.

After a reaction time of 6 hours no oxidation products can be detected (HPLC) in the reaction solution. The 6-hydroxy-2-isopropylnaphthalene employed is not oxidized under the conditions indicated.

EXAMPLE 2

5 g of 4-methylphenol (purity: 99%, HPLC), dissolved in 40 g of acetic anhydride, are put into a 100 ml four-necked flask equipped with a stirrer, a thermometer, a reflux condenser and a gas inlet frit, 3 drops of hydrobromic acid (48%) are added with stirring, and the mixture is then heated to 110° C. After a reaction time of 30 minutes at this temperature, the oxygen supply is started at a rate of 80 ml/minute and, at the same time, 0.25 g of cobalt(II) acetate tetrahydrate and 0.29 g of manganese(II) bromide tetrahydrate are added to the reaction solution. At this time the ratio by weight of acetic acid to acetic anhydride is about 1:4.

It is also possible to add a so-called initiator, for example 0.1 g of di-tert-butyl peroxide, in order to accelerate the initiation of the oxidation.

The reaction is terminated after 6 hours by switching off the supply of oxygen. The ratio by weight of acetic acid to acetic anhydride increases during the reaction to 1:1. The ratio by weight of the compound of the formula (8) to the compound of the formula (7) (R=CH$_3$) is 1.6:1. The reaction mixture is cooled to room temperature. The 4-acetoxybenzoic acid which is precipitated is separated off, washed with water and dried. Yield: 4.1 g (50%), purity: 99% (HPLC). The filtrate, which is saturated at room temperature with the reaction products of the formulae (7) and (8), can be re-used as the reaction medium (Example 3).

EXAMPLE 3

5 g of 4-methylphenol, dissolved in 10 g of acetic anhydride, are acetylated as described in Example 2. The reaction mixture is combined with the filtrate obtained in the reaction according to Example 2. The mixture is heated to 110° C., 0.1 g of di-tert-butyl peroxide are added and the oxygen supply is started at a rate of 80 ml/minute. After 6 hours the reaction is terminated by switching off the supply of oxygen, and the reaction mixture is cooled to room temperature. 8.6 g of 4-acetoxybenzoic acid are precipitated. Before cooling, the following ratios by weight are determined in the reaction mixture: acetic acid to acetic anhydride=3:1 and compound of the formula (8) to compound of the formula (7)=6.1:1. Yield: 8.6 g, purity 98% (HPLC). The yield is over 100% of theory (about 106%), since an additional fraction of 4-acetoxybenzoic acid is precipitated from the filtrate according to Example 2, which has been used here (this is due to the higher ratio of acetic acid to acetic anhydride).

The reaction can also be carried out without the addition of 0.1 g of di-tert-butyl peroxide.

EXAMPLE 4

5 g of 4-methylphenol are acetylated as described in Example 2, but using only 10 g of acetic anhydride and in the course of a reaction time of 1.5 hours. After the acetylation the ratio by weight of acetic acid to acetic anhydride is 1.4:1. When the acetylation is complete, 30 g of acetic acid are added and the oxidation reaction is carried out as in Example 2. After a reaction time of 6 hours it is no longer possible to detect an appreciable amount of acetic anhydride in the reaction mixture. When the reaction has been terminated, the mixture is cooled to room temperature and the precipitated 4-acetoxybenzoic acid is separated off, washed with water and then dried. Yield: 4.7 g (57%). Purity: 99% (HPLC).

The filtrate, which is saturated with the reaction product, is re-used in Example 5.

EXAMPLE 5

5 g of 4-methylphenol are acetylated as described in Example 4. The resulting reaction mixture combined with the filtrate obtained in the reaction according to Example 4. The mixture is heated to 110° C., 0.1 g of di-tert-butyl peroxide is added and the oxygen supply is started at a rate of 80 ml/minute. After 3 hours it is still not possible to observe any oxidation. The reaction only begins after an additional 5 g of acetic anhydride have been added. After a further 6 hours 7.1 g of 4-acetoxybenzoic acid can be obtained by crystallization by cooling the reaction mixture to room temperature. Yield: 7.1 g (86%), purity: 99% (HPLC).

What is claimed is:

1. A process for the preparation of a compound of the formula

HO-Ar-COOH  (1)

in which Ar is a substituted or unsubstituted aromatic ring system, preferably substituted or unsubstituted phenylene or naphthylene, which comprises oxidizing, by means of oxygen or oxygen donors, compounds of the formula RO-Ar-R₁  (2)

in which R is hydrogen or R₂CO- in which R₂ is hydrogen or $C_1$–$C_4$alkyl, $R_1$ is alkyl having 1 to 5 carbon atoms and Ar is as defined above, in an organic solvent at 80° to 130° C., at normal pressure and in the presence of a sufficient amount of an acylating agent to prevent the appearance of free hydroxyl groups during said oxidizing, as well as a cobalt and/or manganese compound and a compound which donates bromide ions, and subsequently hydrolyzing the product in a conventional manner.

2. A process according to claim 1, wherein the compounds of the formula (2) have the formulae

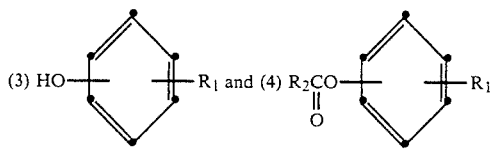

or

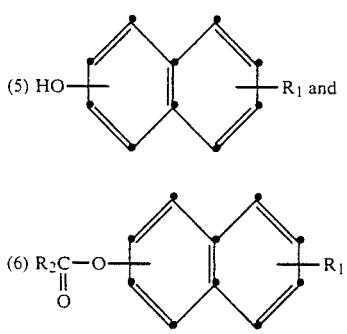

in which $R_1$ is as defined in claim 1 and $R_2$ is hydrogen, $C_1$–$C_1$alkyl, or phenyl.

3. A process according to claim 1, wherein the compounds of the formula (2) have the formulae

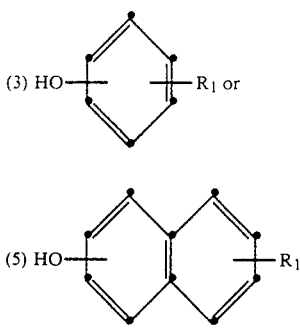

in which $R_1$ is as defined in claim 1.

4. A process according to claim 3, wherein the compounds of the formula (3) are p-methylphenol or p-isopropylphenol and the compounds of the formula (5) are 2-methyl-6-hydroxynaphthalene or 2-isopropyl-6-hydroxynaphthalene.

5. A process according to claim 1, wherein the organic solvents are low-molecular alkylcarboxylic acids having 1 to 5, carbon atoms.

6. A process according to claim 1, wherein the acylating agents are anhydrides of low-molecular alkylcarboxylic acids having 1 to 5, carbon atoms.

7. A process according to claim 1, wherein the oxidation catalysts used are oxides, hydroxides and inorganic or organic salts of cobalt or manganese and mixtures thereof and the compounds which donate bromide ions used are bromine, hydrobromic acid and inorganic bromides or organic bromine compounds.

8. A process according to claim 7, wherein the oxidation catalysts employed are the salts of cobalt or mangenese in amounts of 2 to 4 mole % each, relative to 1 mole of the compounds of the formula (2).

9. A process according to claim 7, wherein the oxidation catalysts employed are mixtures of the salts of cobalt and manganese in amounts of 4 to 8 mole %, relative to 1 mole of the compounds of the formula (2).

10. A process according to claim 1, wherein the oxidation is carried out in the presence of an additional reaction initiator which forms free radicals.

11. A process according to claim 10, wherein organic peroxide or azo compounds are used as reaction initiators.

12. A process according to claim 1, wherein the hydrolysis is carried out in a conventional manner by means of mineral acids, or by means of alkali metal hydroxides.

13. A process according to claim 1, wherein the oxidation is carried out at temperatures from 90° to 130° C.

14. A process according to claim 1, wherein the oxidation is carried out continuously.

* * * * *